US007557256B2

(12) United States Patent
Chang et al.

(10) Patent No.: US 7,557,256 B2
(45) Date of Patent: Jul. 7, 2009

(54) MOLECULAR SIEVE CATALYST COMPOSITION, ITS MAKING AND USE IN CONVERSION PROCESSES

(75) Inventors: Yun-Feng Chang, Houston, TX (US); Stephen N. Vaughn, Kingwood, TX (US); Kenneth R. Clem, Humble, TX (US); Luc R. Martens, Meise (BE); Weiguo Hu, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/818,495

(22) Filed: Jun. 14, 2007

(65) Prior Publication Data
US 2007/0249885 A1    Oct. 25, 2007

Related U.S. Application Data

(62) Division of application No. 10/677,654, filed on Oct. 2, 2003, now Pat. No. 7,241,713.

(51) Int. Cl.
*C07C 1/00* (2006.01)
(52) U.S. Cl. ...................... 585/640; 585/639
(58) Field of Classification Search .......... 585/638–640
See application file for complete search history.

(56) References Cited

U.S. PATENT DOCUMENTS

| 4,062,905 A | 12/1977 | Chang et al. |
| 4,079,095 A | 3/1978 | Givens et al. |
| 4,310,440 A | 1/1982 | Wilson et al. |
| 4,440,871 A | 4/1984 | Lok et al. |
| 4,499,327 A | 2/1985 | Kaiser |
| 4,677,242 A | 6/1987 | Kaiser |
| 4,677,243 A | 6/1987 | Kaiser |
| 4,873,390 A | 10/1989 | Lewis et al. |
| 5,095,163 A | 3/1992 | Barger |
| 5,367,100 A | 11/1994 | Gongwei et al. |
| 5,714,662 A | 2/1998 | Vora et al. |
| 6,166,282 A | 12/2000 | Miller |

FOREIGN PATENT DOCUMENTS

WO        WO 02/05952 A2 *   1/2002

* cited by examiner

*Primary Examiner*—In Suk Bullock

(57) ABSTRACT

This invention provides methods of making molecular sieve catalyst particles, molecular sieve slurries that can be used in such methods, molecular sieve catalyst compositions and their use in catalytic hydrocarbon conversion processes. In one of its aspects, the invention provides a method of making molecular sieve catalyst particles, the method comprising the steps of: a) providing a solution or suspension of an aluminum-containing inorganic oxide precursor in a liquid medium; b) combining the solution or suspension of aluminum-containing inorganic oxide precursor with a molecular sieve, and optionally other formulating agents, to form a catalyst formulation slurry; c) aging the catalyst formulation slurry to generate in said slurry a percentage, or increase in said slurry the existing percentage, of aluminum atoms of the aluminum-containing precursor in the form of oligomers having a sharp $^{27}$Al NMR peak at 62-63 ppm; and d) forming molecular sieve catalyst particles from the catalyst formulation slurry. The catalyst compositions obtained by the methods of the present invention have improved attrition resistance, and are particularly useful in hydrocarbon conversion processes.

5 Claims, 1 Drawing Sheet

MOLECULAR SIEVE CATALYST COMPOSITION, ITS MAKING AND USE IN CONVERSION PROCESSES

This application is a divisional of U.S. Patent application Ser. No. 10/677,654, Oct. 2, 2003 now U.S. Pat. No. 7,241, 713 which is fully incorporated herein by reference.

FIELD OF THE INVENTION

The present invention relates to a molecular sieve catalyst composition, to a method of making or forming the molecular sieve catalyst composition, and to a conversion process using the catalyst composition.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in a variety of processes for making plastics and other chemical compounds.

The petrochemical industry has known for some time that oxygenates, especially alcohols, are convertible into light olefin(s). There are numerous technologies available for producing oxygenates including fermentation or reaction of synthesis gas derived from natural gas, petroleum liquids, carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Syngas production processes are well known, and include conventional steam reforming, autothermal reforming, or a combination thereof.

Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor. The preferred methanol conversion process is generally referred to as a methanol-to-olefin(s) process, where methanol is converted to primarily ethylene and/or propylene in the presence of a molecular sieve.

Molecular sieves are porous solids having pores of different sizes such as zeolites or zeolite-type molecular sieves, carbons and oxides. The most commercially useful molecular sieves for the petroleum and petrochemical industries are known as zeolites, for example aluminosilicate molecular sieves. Zeolites in general have a one-, two- or three-dimensional crystalline pore structure having uniformly sized pores of molecular dimensions that selectively adsorb molecules that can enter the pores, and exclude those molecules that are too large.

There are many different types of molecular sieves well known to convert a feedstock, especially an oxygenate containing feedstock, into one or more olefin(s). For example, U.S. Pat. No. 5,367,100 describes the use of a well known zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; and U.S. Pat. No. 4,310,440 describes producing light olefin(s) from an alcohol using a crystalline aluminophosphates, often represented by $ALPO_4$.

One of the most useful molecular sieves for converting methanol to olefin(s) is a silicoaluminophosphate molecular sieve. Silicoaluminophosphate (SAPO) molecular sieves contain a three-dimensional microporous crystalline framework structure of $[SiO_2]$, $[AlO_2]$ and $[PO_2]$ corner sharing tetrahedral units. SAPO synthesis is described in U.S. Pat. No. 4,440,871, which is herein fully incorporated by reference. SAPO is generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, is shown in U.S. Pat. Nos. 4,499,327, 4,677,242, 4,677, 243, 4,873,390, 5,095,163, 5,714,662 and 6,166,282, all of which are herein fully incorporated by reference.

Typically, molecular sieves are formed into molecular sieve catalyst compositions to improve their durability in commercial conversion processes. The collisions within a commercial process between catalyst composition particles themselves, the reactor walls, and other reactor systems cause the particles to breakdown into smaller particles called fines. The physical breakdown of the molecular sieve catalyst composition particles is known as attrition. Fines often exit the reactor in the effluent stream resulting in problems in recovery systems. Catalyst compositions having a higher resistance to attrition generate fewer fines, less catalyst composition is required for conversion, and longer life times result in lower operating costs.

Molecular sieve catalyst compositions are formed by combining a molecular sieve and a matrix material usually in the presence of a binder. The purpose of the binder is to hold the matrix material, often a clay, to the molecular sieve. The use of binders and matrix materials in the formation of molecular sieve catalyst compositions is well known for a variety of commercial processes. It is also known that the way in which the molecular sieve catalyst composition is made or formulated affects catalyst composition attrition.

Examples of methods of making catalyst compositions include: U.S. Pat. No. 5,126,298 discusses a method for making a cracking catalyst having high attrition resistance by combining two different clay particles in separate slurries with a zeolite slurry and a source of phosphorous, and spray drying a mixture of the slurries having a pH below 3; U.S. Pat. Nos. 4,987,110 and 5,298,153 relate to a catalytic cracking process using a spray dried attrition resistant catalyst containing greater than 25 weight percent molecular sieve dispersed in a clay matrix with a synthetic silica-alumina component; U.S. Pat. Nos. 5,194,412 and 5,286,369 disclose forming a catalytic cracking catalyst of a molecular sieve and a crystalline aluminum phosphate binder having a surface area less than 20 $m^2/g$ and a total pore volume less than 0.1 cc/g; U.S. Pat. No. 4,542,118 relates to forming a particulate inorganic oxide composite of a zeolite and aluminum chlorhydrol that is reacted with ammonia to form a cohesive binder; U.S. Pat. No. 6,153,552 claims a method of making a catalyst, by drying a slurry of a SAPO molecular sieve, an inorganic oxide sol, and an external phosphorous source; U.S. Pat. No. 5,110, 776 illustrates the formation of a zeolite containing catalytic catalyst by modifying the zeolite with a phosphate containing solution; U.S. Pat. No. 5,348,643 relates to spray drying a zeolite slurry with a clay and source of phosphorous at a pH of below 3; U.S. Pat. No. 6,440,894 discusses a method for steaming a molecular sieve to remove halogen; U.S. Pat. No.

5,248,647 illustrates spray drying a SAPO-34 molecular sieve admixed with kaolin and a silica sol; U.S. Pat. No. 5,346,875 discloses a method for making a catalytic cracking catalyst by matching the isoelectric point of each component of the framework structure to the pH of the inorganic oxide sol; Mäurer, et al, *Aggregation and Peptization Behavior of Zeolite Crystals in Sols and Suspensions*, Ind. Eng. Chem. Vol. 40, pages 2573-2579, 2001 discusses zeolite aggregation at or near the isoelectric point; PCT Publication WO 99/21651 describes making a catalyst by drying a mixture of an alumina sol and a SAPO molecular sieve; PCT Publication WO 02/05950 describes making a catalyst composition of a molecular sieve containing attrition particles with fresh molecular sieve; WO 02/05952 discloses a crystalline metallo-aluminophosphate molecular sieve and a matrix material of an inorganic oxide binder and filler where the molecular sieve is present in an amount less than 40 weight percent relative to the catalyst weight and a preferable weight ratio of the binder to molecular sieve close to 1; U.S. Pat. No. 4,443,553 discusses the addition of aluminum hydroxychloride to an aqueous slurry employed in the preparation of fluid catalytic cracking catalysts in order to reduce the viscosity of the slurry; U.S. Pat. No. 4,987,110 discloses cracking catalysts containing a mixture of clay and a synthetic silica-alumina component derived from a silica sol and aluminum chlorhydroxide.

Although the molecular sieve catalyst compositions described above are useful in hydrocarbon conversion processes, it would be desirable to have an improved molecular sieve catalyst composition having better attrition resistance and commercially desirable operability.

SUMMARY OF THE INVENTION

This invention provides methods of making molecular sieve catalyst particles, molecular sieve slurries that can be used in such methods, molecular sieve catalyst compositions and their use in catalytic hydrocarbon conversion processes such as for the manufacture of one or more olefin(s).

In a first aspect, the invention provides a method of making molecular sieve catalyst particles, the method comprising the steps of: a) providing a solution or suspension of an aluminum-containing inorganic oxide precursor in a liquid medium; b) combining the solution or suspension of aluminum-containing inorganic oxide precursor with a molecular sieve, and optionally other formulating agents, to form a catalyst formulation slurry; c) aging the catalyst formulation slurry to generate in said slurry a percentage, or increase in said slurry the existing percentage, of aluminum atoms of the aluminum-containing precursor in the form of oligomers having a sharp $^{27}Al$ NMR peak at 62-63 ppm; and d) forming molecular sieve catalyst particles from the catalyst formulation slurry.

Preferably, aging is carried out at a temperature and for a period of time such that at least 5 atom %, more preferably 10 atom %, of the aluminum atoms of the aluminum-containing precursor in the catalyst formulation slurry is in the form of oligomers having between 10 and 75 aluminum atoms per molecule.

In another preferred embodiment, at least 6 atom %, preferably 8 atom %, of the aluminum atoms of the aluminum-containing precursor in the catalyst formulation slurry is in the form of oligomers having a sharp $^{27}Al$ NMR peak at 62-63 ppm.

In a second aspect, the invention provides a method of making molecular sieve catalyst particles, the method comprising the steps of: a) preparing a solution or suspension of inorganic oxide precursor in a liquid medium; b) combining the solution or suspension of inorganic oxide precursor with a molecular sieve, and optionally other formulating agents, to form a catalyst formulation slurry; c) aging the suspension of inorganic oxide; and d) forming molecular sieve catalyst particles from the catalyst formulation slurry; wherein said aging is carried out at a temperature and for a duration such that the catalyst formulation slurry has a Relative Binding Efficiency between 1.02 and 1.25. Preferably, aging is carried out at a temperature and for a period of time such that the catalyst formulation slurry has a Relative Binding Efficient between 1.02 and 1.2, preferably 1.18, more preferably 1.15.

In a third aspect, the present invention provides a method of making molecular sieve catalyst particles, the method comprising the steps of: a) preparing a solution or suspension of inorganic oxide precursor in a liquid medium; b) combining the solution or suspension of inorganic oxide precursor with a molecular sieve, and optionally other formulating agents, to form a catalyst formulation slurry; c) aging the catalyst formulation slurry; and d) forming molecular sieve catalyst particles from the catalyst formulation slurry; wherein said aging is carried out at a temperature and for a duration such that the molecular sieve catalyst particles obtained after step d) have an ARI value of less than 1.0, preferably of less than 0.5.

In all three aforementioned aspects of the invention, it is preferred that aging in step c) takes place by maintaining the catalyst formulation slurry at a temperature of from 0° C. to 100° C., more preferably of from 15° C. to 80° C. for a period of at least 2 hours, more preferably for a period of at least 4 hours, even more preferably at least 5 hours and most preferably at least 8 hours. It is also preferred that the solution or suspension of inorganic oxide is not aged before combining with the other formulation slurry ingredients.

In a fourth aspect, the present invention provides method of making molecular sieve catalyst particles, the method comprising the steps of: a) providing a solution or suspension of inorganic oxide precursor in a liquid medium; b) aging the solution or suspension of inorganic oxide precursor, c) combining the solution or suspension of inorganic oxide precursor with molecular sieve, and optionally other formulating agents, to form a catalyst formulation slurry; d) forming molecular sieve catalyst particles from the catalyst formulation slurry; wherein aging is carried out at a temperature and for a duration such that the molecular sieve catalyst particles obtained after step d) have an ARI value of less than 1.0, preferably of less than 0.5.

In this fourth aspect of the invention, it is preferred that the catalyst formulation slurry is maintained at a temperature of from 15° C. to 50° C. for a period of not more than 12 hours, preferably not more than 8 hours, before forming the molecular sieve catalyst particles in step d).

Also, in this fourth aspect of the invention, aging of the inorganic oxide precursor solution or suspension is preferably carried out by maintaining the solution or suspension of inorganic oxide at a temperature of from 10° C. to 80° C. for a period of at least 1 hours, preferably for a period of at least 1.5 hours, more preferably for a period of at least 2 hours, even more preferably for a period of at least 3 hours, most preferably for a period of at least 4 hours. More preferably, the solution or suspension of inorganic oxide is maintained is of from 15° C. to 70° C., preferably of from 20° C. to 50° C.

In yet another preferred embodiment of all four aforementioned aspects of the invention, it is preferred that forming the catalyst particles is performed by spray drying and that the method comprises the step of calcining the molecular sieve catalyst particles before catalytic use.

Also, for all four aforementioned aspects of the invention, the preferred inorganic oxide precursor comprises an aluminum oxide precursor and/or a zirconium oxide precursor, and is more preferably an aluminum chlorohydrate or an aluminum-zirconium chlorohydrate.

In a separate embodiment of all four aforementioned aspects of the invention, the preferred liquid medium is water.

In a fifth aspect, the present invention provides a catalyst formulation slurry comprising (a) molecular sieve particles; (b) a hydrolyzed form of aluminum oxide; (c) water; (d) optionally, matrix particles; wherein at least 5 atom %, preferably at least 6 atom %, more preferably at least 10 atom % of the hydrolyzed form of aluminum oxide is in the form of oligomers having a sharp $^{27}$Al NMR peak at 62-63 ppm Preferably, the catalyst formulation slurry further comprises a hydrolyzed form of zirconium oxide.

In all five aforementioned aspects of the invention, it is preferred that the catalyst formulation slurry further contains a matrix material, preferably a clay, more preferably kaolin clay.

In another embodiment of all five aforementioned aspects of the invention, it is preferred that the catalyst formulation slurry has a viscosity of from 1.0 to 10.0 Pa-s, preferably of from 1.2 to 9.5 Pa-s, when measured at a temperature between 23° C. and 30° C., using a Brookfield LV viscometer, with a #3 spindle at 10 rpm.

In a sixth aspect, the present invention provides a molecular sieve catalyst comprising a silicoaluminophosphate molecular sieve; aluminum oxide; zirconium oxide; and a clay; wherein the catalyst has an ARI of less than 1.0, preferably less than 0.7, more preferably less than 0.5, most preferably less than 0.2. Preferably the catalyst has having an aluminum to zirconium atomic ratio of from 0.1 to 20, preferably of from 2.0 to 15, more preferably of from 3.0 to 10.0.

The present invention also relates to the use of the catalysts of the present invention, or made by any method of the present invention in the conversion of hydrocarbon feedstocks.

In all aspects of the invention, the molecular sieve is preferably a metalloaluminophosphate molecular sieve.

DETAILED DESCRIPTION OF THE INVENTION

Introduction

Figure 1:
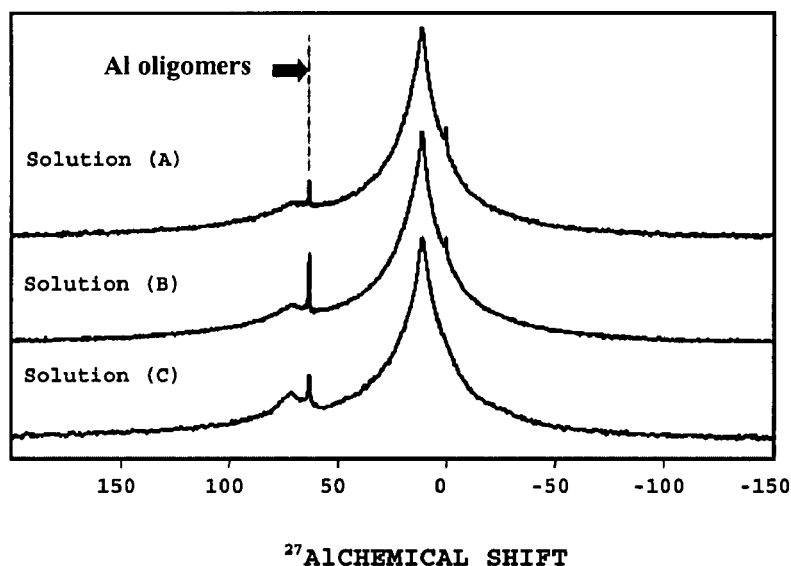
FIG. 1 shows $^{27}$Al NMR spectra of aluminum chlorohydrate (ACH) solutions prepared with and without aging.

The invention is directed toward molecular sieve catalyst compositions, their making and to their use in the conversion of feedstocks into one or more olefin(s).

The molecular sieve catalyst compositions of the present invention are formed from what we shall hereinafter refer to as a catalyst formulation slurry. The catalyst formulation slurry is prepared by combining a solution or suspension of an inorganic oxide precursor, preferably an aluminum oxide or an aluminum-zirconium oxide precursor, with a molecular sieve, optionally in the presence of at least another formulating agent. The slurry then goes through a forming process to produce shaped products, e.g., spray drying. After calcination, molecular sieve catalyst particles are obtained, which have a high resistance to attrition, i.e. physical breakdown.

We have surprisingly found that when the catalyst formulation slurry is submitted to a mild thermal treatment (aging) before formation of the catalyst particles, the molecular sieve catalyst particles are more resistant to attrition than when the catalyst formulation slurry is not aged before formation of the catalyst particles. Also, we have surprisingly found that, if the solution or suspension of inorganic oxide precursor is submitted to a mild thermal treatment (aged) before forming the catalyst formulation slurry, the molecular sieve catalyst particles are more resistant to attrition than when the solution or suspension of inorganic oxide is not aged. In addition, we have found that, when the solution or suspension of inorganic oxide precursor is submitted to a mild thermal treatment (aged) before forming the catalyst formulation slurry, aging of the catalyst formulation slurry should be prevented in order to obtain catalyst particles with highest attrition resistance.

Without wishing to be bound to any theory, when appropriate aging of the solution or suspension of inorganic oxide or appropriate aging of the catalyst formulation slurry is applied, there appears to be an ideal distribution of reactive ionic species in the catalyst formulation slurry, that determines the binding efficiency of the inorganic oxide precursors during the catalyst formulation process. For example, with precursors of aluminum oxide and precursors of aluminum-zirconium oxides, various hydrated forms of aluminum ions, zirconium ions, aluminum hydroxide, zirconium hydroxide, aluminum oxide and zirconium oxide are believed to be present in water solutions or suspensions. Various forms of aluminum compounds are present in the liquid phase, such as oligomeric forms of aluminum containing from 2 to several hundred aluminum atoms per molecule. Various forms of zirconium compounds are present in the liquid phase, such as oligomeric forms of zirconium containing from 2 to several hundreds of zirconium atoms per molecule. The distribution of oligomers depends on several factors including, but not limited to, the aluminum oxide precursor concentration, temperature, the pH, mixing, treatment history, and the ionic strength.

The present invention provides methods by which an optimal distribution of reactive ionic species is obtained in the catalyst formulation slurry, during the catalyst formulation process. The distribution of reactive ionic species, preferably reactive aluminum species, is optimal in that the catalyst formulation slurry yields molecular sieve catalyst particles with higher attrition resistance than when aging according to the invention is not applied.

Catalyst Formulation Slurries

In the context of the present invention, the molecular sieves synthesized above are used in commercial catalytic processes. For this purpose, they are made or formulated into molecular sieve catalyst particles. Molecular sieve catalyst formulation involves making a catalyst formulation slurry, which is then formed into catalyst particles. In the context of the present invention, the molecular sieve-containing slurry which is formed into catalyst particles shall be referred to as the catalyst formulation slurry.

The catalyst formulation slurry is made by combining the synthesized molecular sieve(s) with an inorganic oxide precursor and optionally with a matrix material and/or other formulating agents. In an embodiment, the catalyst formulation slurry is formed by combining an aqueous solution or suspension of an inorganic oxide precursor with a molecular sieve under mixing.

Preferably, the molecular sieve is used in a not fully dried state, such as a filter cake obtained after molecular sieve synthesis, often referred to as a wet filter cake. In another, but less preferred, embodiment, the molecular sieve is fully dried, and optionally calcined, before combining with the solution or suspension of inorganic oxide precursor.

The catalyst formulation slurry may also contain uncalcined molecular sieve-containing catalyst particles, which are recycled in the formulation process, as described in PCT publication No. WO 02/05950, U.S. Pat. Nos. 6,605,749, 6,541,415, 6,509,290 and US Application publication No. 2003/0135079, all incorporated herewith by reference.

There are many inorganic oxide precursors that are useful according to the present invention, non-limiting examples of which include various types of hydrated alumina, silicas, and/or other inorganic oxide sol. Examples of preferred inorganic oxide precursors are alumina precursors, more preferably aluminum chlorohydrate and aluminum-zirconium chlorohydrate. The inorganic oxide precursor used according to the present invention, is converted into an inorganic oxide during the process for manufacturing molecular sieve catalyst particles. During the catalyst manufacturing process, the inorganic oxide precursor acts like glue, binding the synthesized molecular sieves and other optional catalyst formulation materials together, particularly after drying, and/or calcination. Upon heating, the inorganic oxide precursor is converted into an inorganic oxide matrix component. For example, an alumina sol (precursor) will convert to an aluminum oxide matrix following heat treatment and a mixed zirconia-alumina sol (precursor) will convert to a mixed aluminum-zirconium oxide.

Aluminum chlorohydrate, also referred to as aluminum chlorhydrol or aluminum hydroxychloride, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. Aluminum chlorohydrate is usually prepared by dissolving either metallic aluminum or hydrated alumina in hydrochloric acid under controlled conditions. Aluminum chlorohydrate is available commercially in different forms, such as solid products, for example, the solid of chemical formula $Al_2(OH)_5Cl \cdot n(H_2O)$ or as pre-prepared, commercially available, aqueous solutions. Other non-limiting examples of useful aluminum oxide precursors that may be used according to this invention include aluminum hexahydrate, aluminum pentachlorohydrate ($Al_2(OH)Cl_5$), aluminum tetrachlorohydrate ($Al_2(OH)_2Cl_4$), aluminum trichlorohydrate ($Al_2(OH)_3Cl_3$), aluminum dichlorohydrate ($Al_2(OH)_4Cl_2$), aluminum sesquichlorohydrate ($Al_2(OH)_{4.5}Cl_{1.5}$).

In aqueous solution, aluminum chlorohydrate forms monomeric, dimeric, oligomeric and polymeric aluminum species, depending on several factors such as the pH, temperature, treatment history, and the presence of other ionic species or concentration of other ionic species.

Other non-limiting example of binders useful according to the present invention are precursors of aluminum-zirconium oxides. Such precursors include, but are not limited to, aluminum zirconium chlorohydrates, for example, aluminum zirconium trichlorohydrate, aluminum zirconium tetrachlorohydrate, aluminum zirconium pentachlorohydrate, aluminum zirconium octachlorohydrate, aluminum zirconium chlorhydrex, aluminum zirconium chlorhydrex glycine complexes, for example, aluminum zirconium trichlorohydrex glycine complex, aluminum zirconium tetrachlorohydrex glycine complex, aluminum zirconium pentachlorohydrex glycine complex, and aluminum zirconium octachlorohydrex glycine complex. In the absence of glycine, these materials form gels in aqueous solutions. Reheis Chemicals Inc., Berkeley Heights, N.J. produces a variety of aluminum zirconium chlorohydrates. These materials can be prepared from a variety of zirconium starting materials such as zirconyl chloride ($ZrOCl_2$), zirconyl hydroxychloride ($ZrO(OH)Cl$), zirconium hydroxy carbonate paste ($ZrO(OH)(CO_3)0.5$), and combinations of these zirconium starting materials, with a hydrated aluminum solution, such as a solution of aluminum chlorohydrate, aluminum hexahydrate, aluminum sesquichlorohydrate or aluminum dichlorohydrate solution, or a solution obtained by combining one or several of these aluminum species solutions. Aluminum zirconium tetrachlorohydrates are used in antiperspirants and deodorants (Joe Parekh, "APD Aluminum Chlorohydrate", in Soap, Perfumery & Cosmetics, July, 2001; Allan H. Rosenberg and John J. Fitzgerald, "Chemistry of Aluminum-Zirconium-Glycine Complexes", in Antiperspirants and Deodorants, 2nd Edition, Revised and Expanded, ed. by Karl Laden, Marcel Dekker, New York, 1999, pp. 137-168.). Products from Reheis include REACH AZP 902, REACH AZP 908, REACH AZP 855, REACH AZZ 902, REACH AZZ 855, and REACH AZN 855.

In concentrated zirconium solutions, cationic polynuclear $Zr^{4+}$ complexes, e.g., $Zr_3(OH)_4^{8+}$, $Zr_3(OH)_5^{7+}$, $Zr_4(OH)_8^{8+}$, rather than mononuclear hydrolysis species, are predominant in the pH range of 0 to 3.

Without wishing to be bound by any particular theory, it is believed that the presence of the zirconium complexes in aluminum zirconium chlorohydrate solutions causes depolymerization of the high-molecular-weight aluminum species together with the formation of aluminum dimer and monomer species. The acid catalyzed depolymerization of the aluminum species is also accomplished by further polymerization of the various zirconium species.

Other non-limiting examples of alumina precursors that can be used as inorganic oxide precursors in the catalyst formulation slurry include one or several of the following: aluminum oxyhydroxide, γ-alumina, boehmite, diaspore, and transitional aluminas such as β-alumina, γ-alumina, δ-alumina, ε-alumina; κ-alumina, and ρ-alumina, aluminum trihydroxide, such as gibbsite, bayerite, nordstrandite, doyelite, and mixtures thereof.

In an embodiment, the inorganic oxide precursor solution or suspension, preferably an alumina or mixed aluminum-zirconium oxide precursor solution, is prepared immediately before catalyst formulation from an inorganic oxide precursor in powder form and water. Such inorganic oxide precursor solutions shall be hereinafter referred to as "fresh" solutions or "not-aged" solutions. In an embodiment, the fresh inorganic oxide precursor solution is not aged before combining with the other catalyst formulation slurry ingredients, i.e. the inorganic oxide precursor solution is maintained at a temperature of from 15° C. to 50° C. for a period of not more than 8 hours, more preferably not more than 6 hours, even more preferably not more than 4 hours and most preferably not more than 2 hours, before combining with the other ingredients used to formulate the catalyst.

The fresh inorganic oxide solution is combined with the molecular sieve to form the catalyst formulation slurry, and then allowed to age before forming the molecular sieve catalyst particles. In this embodiment, aging means submitting the catalyst formulation slurry to a mild thermal treatment, with or without agitation and/or stirring and/or mixing. The duration of the thermal treatment should be sufficient to allow the generation of the reactive ionic species at a sufficient rate and in an amount sufficient to allow the best attrition resistance properties in the catalyst particles.

Conditions of duration and temperature that allow to achieve this result include: maintaining the catalyst formulation slurry at a temperature of from 0° C. to 100° C., preferably of from 10° C. to 90° C., more preferably of from 15° C. to 80° C., most preferably of from 20° C. to 70° C. The duration of this mild thermal treatment can vary, depending on various factors such as the type of inorganic oxide precursor, the concentration of the inorganic precursor and the temperature. The higher the temperature and the lower the concentration in inorganic oxide precursor, the less time will be required to achieve the proper level of aging of the catalyst formulation slurry according to the invention. Periods of aging will typically be at least 2 hours, preferably at least 4 hours, more preferably at least 5 hours, even more preferably at least 8 hours and most preferably at least 10 hours. In a preferred embodiment, aging of the catalyst formulation slurry is performed for not more than 150 hours, preferably not more than 120 hours, most preferably not more than 100 hours. If aging takes place at a temperature of from 30° C. to 50° C., aging of the catalyst formulation preferably takes place for a period of from 4 hours to 80 hours, preferably of from 5 hours to 75 hours, more preferably of from 6 hours to 50 hours, most preferably of from 7 hours to 26 hours.

In a separate embodiment, the inorganic oxide precursor aqueous solution (or suspensions) has been prepared well before combining with the first molecular sieve slurry, i.e. the aluminum chlorohydrate solution has been allowed to age before combining with the first molecular sieve slurry. This would be the case, for example, when commercially available solutions of inorganic oxide precursors are used. In this embodiment, aging of the inorganic oxide precursor aqueous solution means submitting the solution or suspension of inorganic oxide precursor to a mild thermal treatment with or without agitation and/or stirring and/or mixing, before combining the solution of inorganic oxide precursor with the other ingredients used to formulate the catalyst. The duration of this mild thermal treatment should be sufficient to allow the generation of the reactive ionic species at a sufficient rate and in an amount sufficient when the solution or suspension of inorganic oxide precursor is combined with the molecular sieve in the catalyst formulation slurry. Aging should be performed at a temperature and for a period of time sufficient to allow the best attrition resistance properties in the catalyst particles.

Conditions of duration and temperature that allow to achieve this result include: maintaining the solution or suspension of inorganic oxide precursor at a temperature of from 0° C. to 100° C., preferably of from 10° C. to 90° C., more preferably of from 15° C. to 80° C., most preferably of from 20° C. to 70° C. The duration of this mild thermal treatment can vary, depending on various factors such as the type of inorganic oxide precursor, the concentration of the inorganic precursor and the temperature. The higher the temperature and the lower the concentration in inorganic oxide precursor, the less time will be required to achieve the proper level of aging of the solution or suspension of inorganic oxide precursor according to the invention. Periods of aging will typically be at least 2 hours, preferably at least 4 hours, more preferably at least 5 hours and most preferably at least 6 hours. In a preferred embodiment, aging of the solution or suspension of inorganic oxide precursor takes place at a temperature of from 30° C. to 90° C. and for a period of from 4 to 24 hours, preferably at a temperature of from 30° C. to 55° C. and for a period of from 5 to 20 hours.

If the inorganic oxide precursor aqueous solution or suspension has been aged before forming the catalyst formulation slurry, it is preferred that the catalyst formulation slurry not be aged before forming the molecular sieve catalyst particles.

In a preferred embodiment, the inorganic oxide precursor solution or suspension contains from 1% to 80%, preferably from 2% to 75%, more preferably from 4 to 35 wt % of the inorganic oxide precursor, regardless of whether the inorganic oxide solution or suspension has been aged or not before combining with the other catalyst formulation ingredients.

Besides the inorganic oxide precursor, the catalyst formulation slurry of the invention contains at least one molecular sieve and, optionally a matrix material or other formulating agents.

The molecular sieve that can be used in the catalyst formulation process of the present invention vary within wide ranges of composition and structural features.

Molecular sieves have various chemical and physical, framework, characteristics. Molecular sieves have been classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types,* 5th edition, Elsevier, London, England (2001), which is herein fully incorporated by reference.

Molecular sieve materials have 3-dimensional framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition,* Volume 137, pages 1-67, Elsevier Science, B. V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units.

Non-limiting examples of molecular sieves having a molecular framework made of corner-sharing $[SiO_4]$ and $[AlO_4]$ tetrahedral units that can be used include the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Non-limiting examples of molecular sieves having a molecular framework made of corner-sharing [AlO$_4$] and [PO$_4$], optionally with [SiO$_4$], tetrahedral units that can be used in the catalyst formulation processes of the invention include those described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (Li-APSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference. Other molecular sieves are described in R. Szostak, Handbook of Molecular Sieves, Van Nostrand Reinhold, New York, N.Y. (1992), which is herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and metal substituted ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthamides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

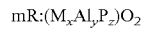

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthamide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Desirably, the molecular sieves of this invention are metalloaluminophosphate that contain Si and Al, at a Si/Al atomic ratio of not greater than about 0.5, preferably not greater than about 0.3, more preferably not greater than about 0.2, still more preferably not greater than about 0.15, and most preferably not greater than about 0.1. Preferably, the metalloaluminophosphate molecular sieves contain Si and Al at an atomic ratio of at least about 0.005, more preferably at least about 0.01.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. AEI/CHA intergrowths are described in the U.S. patent application Ser. No. 09/924,016 filed Aug. 7, 2001 and PCT WO 98/15496 published Apr. 16, 1998, both of which are herein fully incorporated by reference. For example, SAPO-18, ALPO-18 and RUW-18 have an AEI framework-type, and SAPO-34 has a CHA framework-type. In another embodiment, the molecular sieve comprises at least one intergrown phase of AEI and CHA framework-types.

Optionally, the catalyst formulation slurry also contains one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals; non-active, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin; most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.05 µm to about 0.6 µm with a $d_{90}$ particle size of less than about 1 µm.

The amount of inorganic oxide precursor (when expressed as inorganic oxide) in the catalyst formulation slurry is from about 2% by weight to about 35% by weight, preferably from about 3% by weight to about 28% by weight, and more preferably from about 4% by weight to about 24% by weight, based on the total weight of the inorganic oxide precursor (when expressed as inorganic oxide), the molecular sieve and matrix material, excluding the liquid.

Non-limiting examples of other optional formulation agents that can be present in the catalyst formulation slurry include surfactants, for example, Calloway 3330 from Vulcan Chemicals Inc., Montgomery, Ala., or other water soluble polymers, for example, polyvinyl provilidone (PVP)-K90, from BASF America, Rockway, N.J.

At all stages of the molecular sieve catalyst formulation process, mixing, and preferably, vigorous mixing is needed to produce a substantially homogeneous mixture. In one embodiment, the slurry is subjected to high shear for a period of time sufficient to produce the desired slurry texture, size and/or size distribution of catalyst formulation slurry components in the form of solid particles. Suitable means for subjecting the slurry to milling including colloid mills, inline mixers, and the like.

While the present invention is illustrated with slurries of molecular sieves in water, other liquids can used in partial or complete replacement of water. Non-limiting examples of suitable liquids include one or a combination of water, alcohols, ketones, aldehydes, and/or esters. The most preferred liquid is water.

To ensure the quality of the catalyst formulation slurry before forming catalyst particles of the invention, the pH, surface area, solid content and density of the slurry are also preferably monitored using respectively, for example, a Cole Palmer pH meter, Micromeritics Gemini 9375 surface area instrument available from Micometrics Instrument Corporation, Norcross, Ga., CEM MAS 700 microwave muffle furnace for solid content determination available from CEM Corporation, Mathews, N.C. and any standard volume measuring device that can be accurately weighed.

Aging during the catalyst formulation process of the present invention results in catalyst formulation slurries having relatively high viscosity. Preferably, before forming the catalyst particles, the catalyst formulation slurry has a viscosity of from 1,000 centipoise to 10,000 centipoise (1.0 to 10 Pa-s), more preferably of from 1,200 centipoise to 9,500 centipoise (1.2-9.5 Pa-s), when measured at a temperature between 23 and 30° C., as measured using a Brookfield LV-DVE viscometer with a #3 spindle at 10 rpm.

In one embodiment, the sequence of adding each individual component, the molecular sieve, inorganic oxide precursor, matrix material, and other ingredient, is performed in a specific order. Sequence of addition is most important when the surface of the different particles, whether these are of the molecular sieve, the binder, or the matrix materials, have opposite charges, negative and positive, or different charge densities. As a general rule, after size reduction is completed, if necessary, the last step is the addition and mixing of the opposite charged particles. In one preferred embodiment, it is best to add the component selected from the molecular sieve, the binder or the matrix material, having a higher charge density per unit mass to a component having a lower charge density per unit mass.

Molecular Sieve Catalyst Particles

The catalyst formulation slurry is formed into catalyst particles, using a forming unit. In a preferred embodiment, the forming unit is a spray dryer. Typically, the forming unit is maintained at a temperature sufficient to evaporate most of the liquid from the catalyst formulation slurry, and form the resulting molecular sieve catalyst particles. The resulting catalyst composition when formed in this way preferably takes the form of microspheres.

When a spray dryer is used as the forming unit, typically, the catalyst formulation slurry is fed to the spray drying volume with a drying gas with an average inlet temperature ranging from 100° C. to 55° C., and a combined outlet temperature ranging from 50° C. to about 225° C. In an embodiment, the average diameter of the spray dried formed catalyst composition is from about 10 µm to about 300 µm, preferably from about 20 µm to about 250 µm, more preferably from about 30 µm to about 150 µm, and most preferably from about 40 µm to about 120 µm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psig to 2000 psig (690 kPag to 13790 kPag). In another embodiment, the slurry is co-fed through a single nozzle or multiple nozzles along with an atomization fluid such as air, steam, flue gas, or any other suitable gas with a pressure drop in the range of from 1 psig to 150 psig (6.9 kPag to 1034 kPag).

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve catalyst composition in a microspherical form.

Generally, the size of the microspheres is controlled to some extent by the solids content of the slurry. However, control of the size of the catalyst composition and its spherical characteristics are also controllable by varying the slurry feed properties and conditions of atomization.

Other methods for forming a molecular sieve catalyst composition is described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition contains from about 1% to about 99%, preferably from about 10% to about 90%, more preferably from about 10% to about 80%, even more preferably from about 20% to about 70%, and most preferably from about 20% to about 60% by weight of the molecular sieve based on the total weight of the molecular sieve catalyst composition.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof. In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 1 minutes to about 10 hours, preferably 15 minutes to about 2 hours.

In one embodiment, the attrition resistance of a molecular sieve catalyst composition is measured using an Attrition Rate Index (ARI), measured in weight percent catalyst composition attrited per hour. An apparatus that can be used for this purpose is as described in S. A. Weeks and P. Dumbill, in Oil & Gas Journal, pages 38 to 40, 1987, which is herein fully incorporated by reference. A detailed description of the test is provided in the examples below, that illustrate the present invention.

In one embodiment, the molecular sieve catalyst composition or formulated molecular sieve catalyst composition has an ARI less than 5 weight percent per hour, preferably less than 2 weight percent per hour, more preferably less than 1 weight percent per hour and most preferably less than 0.5 weight percent per hour. In one embodiment, the molecular sieve catalyst composition or formulated molecular sieve catalyst composition has an ARI in the range of from 0.1 weight percent per hour to less than 5 weight percent per hour, more preferably from about 0.2 weight percent per hour to less than 3 weight percent per hour, and most preferably from about 0.2 weight percent per hour to less than 2 weight percent per hour.

Process for Using the Molecular Sieve Catalyst Compositions

The catalyst compositions described above are useful in a variety of processes including cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene; polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumene or with long chain olefins; transalkylation, of for example a combination of aromatic and polyalkylaromatic hydrocarbons; dealkylation; hydrodecyclization; disproportionation, of for example toluene to make benzene and paraxylene; oligomerization, of for example straight and branched chain olefin(s); and dehydrocyclization.

Preferred processes include processes for converting naphtha to highly aromatic mixtures; converting light olefin(s) to gasoline, distillates and lubricants; converting oxygenates to olefin(s); converting light paraffins to olefins and/or aromatics; and converting unsaturated hydrocarbons (ethylene and/or acetylene) to aldehydes for conversion into alcohols, acids and esters.

The most preferred process of the invention is a process directed to the conversion of a feedstock to one or more olefin(s). Typically, the feedstock contains one or more aliphatic-containing compounds such that the aliphatic moiety contains from 1 to about 50 carbon atoms, such as from 1 to 20 carbon atoms, for example from 1 to 10 carbon atoms, and particularly from 1 to 4 carbon atoms.

Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

The catalyst composition of the invention is particularly useful in the process that is generally referred to as the gas-to-olefins (GTO) process or alternatively, the methanol-to-olefins (MTO) process. In this process, an oxygenated feedstock, most preferably a methanol-containing feedstock, is converted in the presence of a molecular sieve catalyst composition into one or more olefin(s), preferably and predominantly, ethylene and/or propylene.

Using the catalyst composition of the invention for the conversion of a feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

In addition to the oxygenate component, such as methanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The present process can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec. See for example U.S. patent application Ser. No. 09/708,753 filed Nov. 8, 2000, which is herein incorporated by reference.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the process is conducted as a fluidized bed process or high velocity fluidized bed process utilizing a reactor system, a regeneration system and a recovery system.

In such a process the reactor system conveniently includes a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of fresh feedstock fed as a liquid and/or a vapor to the reactor system is in the range of from 0.1 weight percent to about 85 weight percent, such as from about 1 weight percent to about 75 weight percent, more typically from about 5 weight percent to about 65 weight percent based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 150° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture), which is herein fully incorporated by reference.

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds*, Grace, Avidan and Knowlton, eds., Blackie, 1997 (336-337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, a wash tower often referred to as a caustic wash tower and/or quench tower, absorbers, adsorbers, membranes, ethylene (C2) splitter, propylene (C3) splitter and butene (C4) splitter.

Various recovery systems useful for recovering olefin(s), such as ethylene, propylene and/or butene, are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249-271 and 894-899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which are herein incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Typically, in converting one or more oxygenates to olefin(s) having 2 or 3 carbon atoms, a minor amount hydrocarbons, particularly olefin(s), having 4 or more carbon atoms is also produced. The amount of $C_4+$ hydrocarbons is normally less than 20 weight percent, such as less than 10 weight percent, for example less than 5 weight percent, and particularly less than 2 weight percent, based on the total weight of the effluent gas withdrawn from the process, excluding water. Typically, therefore the recovery system may include one or more reaction systems for converting the $C_4+$ impurities to useful products.

Non-limiting examples of such reaction systems are described in U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all fully herein incorporated by reference.

The preferred light olefin(s) produced by any one of the processes described above are high purity prime olefin(s) products that contain a single carbon number olefin in an amount greater than 80 percent, such as greater than 90 weight percent, such as greater than 95 weight percent, for example at least about 99 weight percent, based on the total weight of the olefin.

In one practical embodiment, the process of the invention forms part of an integrated process for producing light olefin(s) from a hydrocarbon feedstock, preferably a gaseous hydrocarbon feedstock, particularly methane and/or ethane. The first step in the process is passing the gaseous feedstock, preferably in combination with a water stream, to a syngas production zone to produce a synthesis gas (syngas) stream, typically comprising carbon dioxide, carbon monoxide and hydrogen. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material. Preferably synthesis gas stream is produced via steam reforming of natural gas.

The next step in the process involves contacting the synthesis gas stream generally with a heterogeneous catalyst, typically a copper based catalyst, to produce an oxygenate containing stream, often in combination with water. In one embodiment, the contacting step is conducted at temperature in the range of from about 150° C. to about 450° C. and a pressure in the range of from about 5 MPa to about 10 MPa.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fuel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, can then be used as a feedstock in a process to produce light olefin(s), such as ethylene and/or propylene. Non-limiting examples of this integrated process are described in EP-B-0 933 345, which is herein fully incorporated by reference.

In another more fully integrated process, that optionally is combined with the integrated processes described above, the olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above. However, the preferred polymerization catalysts are the Ziegler-Natta, Phillips-type, metallocene, metallocene-type and advanced polymerization catalysts, and mixtures thereof.

In a preferred embodiment, the integrated process comprises a process for polymerizing one or more olefin(s) in the presence of a polymerization catalyst system in a polymerization reactor to produce one or more polymer products, wherein the one or more olefin(s) have been made by converting an alcohol, particularly methanol, using a molecular sieve catalyst composition as described above. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

EXAMPLES

In order to provide a better understanding of the present invention including representative advantages thereof, the following examples are offered.

Amounts and Proportions on a Calcined Basis

Constituents of a mixture used for formulating catalysts will generally contain volatile components, including, but not limited to, water and, in the case of molecular sieve, organic template. It is common practice to describe the amount or proportion of these constituents as being on a "calcined basis". Calcination involves heating a material in the presence of air at an elevated temperature sufficient to dry and remove any contained volatile content (for example at 650° C. for one or more hours). On a "calcined basis" is defined, for the purposes of the current invention, as the amount or fraction of each component remaining after it has been mathematically reduced to account for losses in weight expected to occur if the component had been calcined. The term LOI (Loss-On-Ignition) is used herein interchangeably with the fractional loss during calcination, on a "calcined basis". Thus, 10 grams of a component containing 25% volatiles would be described as "7.5 g on a calcined basis" with an LOI of 2.5 g or 25 wt %.

Methods.

Attrition Resistance Test

The attrition resistance of a molecular sieve catalyst composition is measured using an Attrition Rate Index (ARI), measured in weight percent catalyst composition attrited per hour. An apparatus such as described in S. A. Weeks and P. Dumbill, in Oil & Gas Journal, pages 38 to 40, 1987, which is herein fully incorporated by reference. ARI is measured by adding 6.0 g of catalyst composition having a particles size ranging from about 53 microns to about 125 microns to a hardened steel attrition cup. Approximately 23,700 cc/min of nitrogen gas is bubbled through a water-containing bubbler to humidify the nitrogen. The wet nitrogen passes through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent the catalyst composition that has broken apart through attrition. The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst charged to the attrition cup expressed on per hour basis is the ARI, in weight percent per hour (wt. %/hr). ARI is represented by the formula: ARI=C/(B+C)/D multiplied by 100%, wherein B is weight of catalyst composition left in the cup after the attrition test, C is the weight of collected fine catalyst particles after the first hour of attrition treatment, and D is the duration of treatment in hours after the first hour attrition treatment. A higher ARI means a higher attrition rate or a catalyst less resistant to physical breakdown.

Viscosity

Viscosity of the catalyst formulation slurries was measured using a Brookfield LV viscometer from Brookfield Engineering Laboratories Inc., Middleboro, Mass., using a #3 spindle at a variety of shear rate, ranging, for example, from 10 RPM to 100 RPM. All measurements were carried at room temperature. The viscometer was first calibrated with calibration standards having viscosity of 500 cps, 1000 cps, and 3000 cps (respectively 0.5, 1.0 and 3.0 Pa-s) before taking measurement of the slurry samples. These calibration standards were certified from Brookfield Engineering Laboratories Inc., Middleboro, Mass.

$^{27}$Al NMR $^{27}$Al NMR measurements were conducted using a Bruker DSX 500 NMR spectrometer, with a $^1$H frequency of 500.13 MHz and an $^{27}$Al frequency of 130.31 MHz, using a single 90 ($^{27}$Al) pulse and a recycle delay of 1 second.

Speciation of Aluminum Chlorohydrate (ACH) Measured by HPLC

Aluminum chlorohydrates (ACH) are stable, high molecular weight inorganic polymers that do not form a continuous molecular weight distribution. This lack of suitable molecular weight references and the polymer's multiple charge makes their identification difficult.

In the preparation of ACH, a wide spectrum of basic aluminum polymeric salts of different properties exists, which undergo slow and continuing changes as a function of method of preparation, temperature, age, pH, aluminum to chloride ratio. All these factors determine the structure and reactivity of these species.

HPLC/GPC (high pressure liquid chromatography/gel permeation chromatography) is used to characterize these changes.

With this technique, the various polymeric species elute from the column based on their size, with the largest polymers eluting more quickly than the smallest polymers.

HPLC analysis of ACH solutions was conducted using a Waters HPLC (Waters Corporation, Milford, Mass.) with a Phenonmenex Maxsil RP2 column having pore size of 60 Angstrom and particle size of 5 microns from Phenonmenex Corporation, Torrance, Calif. The analysis conditions were: room temperature, 0.01 M nitric acid as mobile phase at a flow rate of 1 ml/min, and using a refractive index (RI) detector for detection.

The chromatogram, RI detector signal in volts as a function of retention time, provides a finger-print of speciation of an ACH solution.

Example 1

Catalyst Formulation Using a Commercial Ach Solution

Example 1.1

A molecular sieve slurry containing 45 wt % solid was prepared according to this procedure: (A) 991.56 g of SAPO-34 molecular sieve (wet filter cake, LOI: 45.54%) were added to 568.55 g of deionized water and mixed at 600-800 rpm for 5-10 minutes using a Yamato Model 2100 homogenizer (Yamato Scientific America Inc., Orangeburg, N.Y.), then mixed using a Silverson L4RT-A high-shear mixer at 6000 rpm (Silverson Machines, Inc., East Longmeadow, Mass.) for 5 minutes to give a first molecular sieve slurry having a pH of 6.5 at 32° C.; (B) 608.94 g of a commercial aluminum chlorohydrate solution, (Reheis Chlorhydrol 50 wt % solution, Lot. # 58204, having an aluminum to chloride atomic ratio of 2.0 and available from Reheis Inc., Berkeley Heights, N.J. was added to slurry (A) under agitation. The resulting mixture was mixed at 600-800 RPM using Yamato homogenizer for 5 minutes, then mixed using Silverson high-shear mixer at 6000 RPM for 5 minutes. The slurry thus obtained had a pH of 3.9 at 26° C.; (C) 767.79 g of USP Ultrafine kaolin clay (Engelhard Corporation, Iselin, N.J.) was added to the slurry obtained in step (B) while mixing at 600 rpm. The mixing rate was increased progressively to 1000 RPM and maintained for 10 minutes resulting in a slurry having a pH of 3.9 at 30° C.; (D) 63.17 g of deionized water were then added to the slurry obtained at step (C) under agitation at 600 RPM, then mixed using the Silverson high-shear mixer at 6000 RPM for 5 minutes. This resulted in a smooth slurry having a pH of 3.9 at 31° C., containing 45 wt % solids (on calcined basis), of which, 40% is SAPO-34, 10.6% is alumina, and 49.4% is clay, hereinafter referred to as Slurry 1. Slurry 1 (750 g) was spray dried, using a Yamato DL-41 spray dryer (Yamato Scientific America, Orangeburg, N.Y.). The spray dryer operated in a down spray mode using an atomization nozzle of 1 mm. The spray drying conditions were: feed rate: 40 g/min; inlet temperature: 350° C.; atomization pressure: 1 bar; carrier gas (nitrogen) flow at 60% of full setting. Spray dry products were collected in a cyclone. They were calcined in a muffle furnace at 650° C. in air for 2 hours to yield Catalyst 1. The catalyst was submitted to an attrition resistance test. Catalyst 1 gave an ARI of 0.44%/hr after calcination.

Example 1.2

A portion of Slurry 1 (1500 g) was kept in a water bath at 40° C. for 16 hours while under constant mixing at 250-350 RPM. After this treatment, water was added to the slurry to make up the amount of water lost due to evaporation followed by a high-shear mixing at 6000 RPM (Silverson high-shear mixer) for 5 minutes. This slurry will be hereinafter referred to as Slurry 2.

A portion of Slurry 2 (750 g) was spray dried using a Yamato DL-41 spray dryer (Yamato Scientific America, Orangeburg, N.Y.) under the same conditions as in Example 1.1. The spray dried products were calcined in a muffle furnace at 650° C. in air for 2 hours to yield Catalyst 2. The catalyst was submitted to an attrition resistance test. Catalyst 2 gave an ARI of 0.67%/hr.

Example 1.3

A portion of the Slurry 2 (750 g) was left at room temperature for three days without mixing. This slurry will be hereinafter referred to as Slurry 3.

A portion of Slurry 3 (750 g) was spray dried using a Yamato DL-41 spray dryer (Yamato Scientific America, Orangeburg, N.Y.) under the same conditions as in Example 1.1. The spray dried products were calcined in a muffle furnace at 650° C. in air for 2 hours to yield Catalyst 3. The catalyst was submitted to an attrition resistance test. Catalyst 3 gave an ARI of 1.36%/hr.

Table 1 summarizes the results of the attrition resistance tests obtained for the catalysts spray dried from Slurries 1, 2 and 3 that have undergone different aging treatments. The results of the attrition resistance test show that slurry 1, that has not undergone any aging or thermal treatment before spray drying, gives the catalyst which is most resistant to attrition. Thermal aging of the slurry (Slurry 2) gives a spray dried catalyst which is less attrition resistance than Catalyst 1. Prolonged slurry aging (Slurry 3) reduces even further catalyst attrition resistance after spray drying.

TABLE 1

Catalyst formulation using a commercial 50 wt % ACH solution.

| Slurry | Aging | Spray Dried catalyst | ARI (%/hr) |
|---|---|---|---|
| Slurry 1 | None | Catalyst 1 | 0.44 |
| Slurry 2 | 40° C., 16 hrs | Catalyst 2 | 0.67 |
| Slurry 3 | 40° C., 16 hrs R.T., 3 days | Catalyst 3 | 1.36 |

Example 2

Catalyst Formulation Using Fresh ACH Solutions

Example 2.1

A slurry containing 45 wt % solid was prepared according to this procedure:

(A) 2988.93 g of a SAPO-34 molecular (wet filter cake, LOI: 45.54%) were added to 1703.84 g of deionized water and mixed at 1500 RPM using a Yamato 4000D mixer (Yamato Scientific America Inc., Orangeburg, N.Y.) for 15 minutes, giving a slurry having a pH value of 6.2 measured at 26° C.;

(B) an aluminum chlorhydrol solution was prepared by adding 869.03 g of Reheis MicroDry aluminum chlorohydrate (Reheis Inc., Berkeley Heights, N.J.) to 859.12 g of deionized water and mixing at 1500 RPM using a Yamato 4000D mixer (Yamato Scientific America Inc., Orangeburg, N.Y.) for 15 minutes followed by a high-shear treatment using the Silverson high shear mixer at 6000 RPM for 10 minutes. This solution had a pH of 3.3 measured at 31° C.

(C) The aluminum chlorhydrol solution prepared in (B) was combined with the SAPO-34 slurry prepared in (A). The resulting mixture was mixed at 1500 RPM using a Yamato 4000D mixer (Yamato Scientific America Inc., Orangeburg, N.Y.) for 15 minutes then mixed using the Silverson high-shear mixer at 6000 RPM for 10 minutes. This resulted in a slurry having a pH value of 4.2 measured at 30° C.

(D) 2302.3 g of USP Ultrafine kaolin clay (Engelhard Corporation, Iselin, N.J.) were added to the slurry prepared at (C) under constant mixing at 250-400 RPM. The resulting slurry was then mixed at 1500 RPM using a Yamato 4000D mixer (Yamato Scientific America Inc., Orangeburg, N.Y.) for 15 minutes followed by a high-shear mixing step using the Silverson mixer at 6000 RPM for 10 minutes.

(E) Deionized water (283.97 g) was added to the slurry prepared at (D). The slurry was then mixed at 1500 RPM for 15 minutes using the Yamato mixer followed by high-shear mixing using the Silverson mixer at 6000 RPM for 10 minutes. This final slurry, hereinafter referred to as Slurry 4, had a pH of 3.8 measured at 36° C. This led to 8000 g of Slurry 4 containing 45 wt % solids (on calcined basis), of which, 40% is SAPO-34, 10.6% is alumina, and 49.4% is clay.

A portion of Slurry 4 (800 g) was spray dried using a Yamato DL-41 spray dryer (Yamato Scientific America, Orangeburg, N.Y.) under the same conditions as in Example 1.1. The spray dried products were calcined in a muffle furnace at 650° C. in air for 2 hours to yield Catalyst 4. The catalyst was submitted to an attrition resistance test. Catalyst 4 gave an ARI of 0.95%/hr.

Example 2.2

A portion of Slurry 4 from Example 2.1 (1500 g) was kept in a water bath at 40° C. for 16 hours while under constant mixing at 250-350 RPM. After this treatment, water was added to the slurry to make up the amount of water lost due to evaporation followed by a high-shear mixing at 6000 RPM (Silverson high-shear mixer) for 5 minutes. This slurry will be hereinafter referred to as Slurry 5.

A portion of Slurry 5 (750 g) was spray dried using a Yamato DL-41 spray dryer (Yamato Scientific America, Orangeburg, N.Y.) under the same conditions as in Example 1. The spray dried products were calcined in a muffle furnace at 650° C. in air for 2 hours to yield Catalyst 5. The catalyst was submitted to an attrition resistance test. Catalyst 2 gave an ARI of 0.38%/hr.

Table 2 summarizes the results of the attrition resistance tests obtained for the catalysts spray dried from Slurries 4 and 5 that have undergone different aging treatments. The results of the attrition resistance test show that Slurry 5, that has undergone aging and/or thermal treatment before spray drying, gives the catalyst which is most resistant to attrition.

TABLE 2

Catalyst formulation using a freshly made 50 wt % ACH solution.

| Slurry | Aging | Viscosity* | Spray Dried catalyst | ART (%/hr) |
|---|---|---|---|---|
| Slurry 4 | None | 4.920 (23.4) | Catalyst 4 | 0.95 |
| Slurry 5 | 40° C., 16 hrs | 6.260 (23) | Catalyst 5 | 0.38 |

*Viscosity in Pa-s, measured at 10 RPM, using a Brookfield LV viscometer, #3 spindle. The measurement temperature in ° C. is indicated between brackets.

Example 3

Catalyst Formulation Using Fresh ZACH Solutions

Example 3.1

A slurry containing 45 wt % solid was prepared according to this procedure: (A) 991.56 g of a SAPO-34 molecular (wet filter cake, LOI: 45.54%) were added to 573.15 g of deionized water and mixed at 700 RPM for 10 minutes using a Yamato 2100 homogenizer (Yamato Scientific America Inc., Orangeburg, N.Y.), then mixed using a Silverson high-shear mixer at 6000 rpm (Silverson Machines, Inc., East Longmeadow, Mass.), giving a slurry having a pH value of 6.9; (B) a zirconium aluminum tetrachlohydrex solution was prepared by adding 285.39 g of Reach AZP-908 Superultrafine activated zirconium aluminum tertrachlorhydrex GL (Reheis Inc., Berkeley Heights, N.J.) to 286.59 g of deionized water and mixing at 700 RPM using the Yamato 2100 mixer for 10 minutes. This solution had a pH of 3.1. (C) The zirconium aluminum tetrachlorhydrex solution prepared in (B) was combined with the SAPO-34 slurry prepared in (A) while mixing at 700 RPM with the Yamato 2100 homogenizer. The resulting mixture was then mixed using the Silverson high-shear mixer at 6000 RPM for 4 minutes. This resulted in a slurry having a pH value of 3.6. (D) 767.7 g of USP Ultrafine kaolin clay (Engelhard Corporation, Iselin, N.J.) were added to the slurry prepared at (C) under mixing at 700 RPM. Mixing at 700 RPM was continued for 10 minutes, resulting in a slurry having a pH of 3.6. (E) The slurry was then submitted to a high-shear mixing step using the Silverson mixer at 6000 RPM for 4 minutes. (F) Deionized water (95.52 g) was added to the slurry prepared at (E). The slurry was then mixed at 700 RPM for 10 minutes using the Yamato mixer followed by high-shear mixing using the Silverson mixer at 6000 RPM for 4 minutes. This final slurry, hereinafter referred to as Slurry 6, contained 45 wt % solids (on a calcined basis), of which, 40% is SAPO-34, 10.6% is zirconia-alumina (4.3 wt % $ZrO_2$ and 6.3 wt % $Al_2O_3$), and 49.4% is clay.

A portion of Slurry 6 (750 g) was spray dried using a Yamato DL-41 spray dryer (Yamato Scientific America, Orangeburg, N.Y.) under the same conditions as in Example 1.1. The spray dried products were calcined in a muffle furnace at 650° C. in air for 2 hours to yield Catalyst 6. The catalyst was submitted to an attrition resistance test. Catalyst 6 gave an ARI of 1.05%/hr.

Example 3.2

A portion of Slurry 6 was kept in a water bath at 40° C. for 16 hours while under constant mixing at 250 RPM. After this treatment, water was added to the slurry to make up the amount of water lost due to evaporation followed by a high-shear mixing at 6000 RPM (Silverson high-shear mixer) for 5 minutes. This slurry will be hereinafter referred to as Slurry 7.

A portion of Slurry 7 was spray dried using a Yamato DL-41 spray dryer (Yamato Scientific America, Orangeburg, N.Y.) under the same conditions as in Example 1.1. The spray dried products were calcined in a muffle furnace at 650° C. in air for 2 hours to yield Catalyst 7. The catalyst was submitted to an attrition resistance test. Catalyst 7 gave an ARI of 0.43%/hr.

Example 3.3

A portion of Slurry 7 was left at room temperature for three days without mixing. This slurry will be hereinafter referred to as Slurry 8.

A portion of Slurry 8 was spray dried using a Yamato DL-41 spray dryer (Yamato Scientific America, Orangeburg, N.Y.) under the same conditions as in Example 1.1. The spray dried products were calcined in a muffle furnace at 650° C. in air for 2 hours to yield Catalyst 8. The catalyst was submitted to an attrition resistance test. Catalyst 8 gave an ARI of 0.20 wt %/hr.

Table 3 summarizes the results of the attrition resistance tests obtained for the catalysts spray dried from Slurries 6, 7 and 8 that have undergone different aging treatments. The results of the attrition resistance test show that Slurry 8, that has undergone thermal treatment and aging before spray drying, gives the catalyst which is most resistant to attrition.

TABLE 3

Catalyst formulation using a freshly made 50 wt % ZACH solution.

| Slurry | Aging | Spray Dried catalyst | ARI (%/hr) |
|---|---|---|---|
| Slurry 6 | None | Catalyst 6 | 1.05 |
| Slurry 7 | 40° C., 16 hrs | Catalyst 7 | 0.43 |
| Slurry 8 | 40° C., 16 hrs R.T., 3 days | Catalyst 8 | 0.20 |

The effect of aging is also illustrated by viscosity and density measurements of Slurries 6, 7 and 8, as shown in Table 4.

Density (specific gravity, in g/cc) measurement of catalyst formulation slurries was conducted using a Paul N. Gardner U.S. Standard Weight Per Gallon Cup, Gardco Cup 83.2, having a volume of 83.2 cc from Paul N. Gardner Company Inc., Pompano Beach, Fla. according to ASTM D1475.

The net weight, W, in grams of the content of the cup is converted to Pounds per British Gallon (PBG) by multiplying a factor 0.1, $PBG = W*0.1$ in lb/GL For example, a slurry sample giving a W of 123.82 g has a PBG of 12.38 lb/GL. Specific gravity (SG) or density is obtained by converting PBG multiplying by a factor, 0.1202, $SG = PBG*0.1202$ in g/cc For example, a slurry sample giving a PBG of 12.382 has a density of 1.49 g/cc.

Viscosity was measured as described previously in this text, on a Brookfield viscometer using spindle No. 3.

TABLE 4

Viscosity and density measurements.

| Slurry No. | Density g/cc | Viscosity* at the following shear rates: | | | | |
|---|---|---|---|---|---|---|
| | | 100 | 60 | 30 | 20 | 10 |
| Slurry 6 | 1.47 | 0.324 (27.1) | 0.424 (27.1) | 0.648 (27.1) | 0.798 (27.1) | 1.080 (27.1) |
| Slurry 7 | 1.51 | 1.068 (24.6) | 1.416 (24.6) | 2.152 (24.6) | 2.766 (24.6) | 4.280 (24.6) |
| Slurry 8 | 1.47 | n.a. (28.5) | n.a. (28.5) | 3.392 (28.5) | 4.626 (28.5) | 7.670 (28.5) |

*Viscosity in Pa-s, measured at 10 RPM, using a Brookfield LV viscometer, #3 spindle. The measurement temperature in ° C. is indicated between brackets
n.a.: Not available - The instrument did not report any measurement value.

The results in Table 4 show that aging increases the viscosity of the catalyst formulation slurry, while the density does not change significantly. The slurry with the highest viscosity produces catalyst with highest attrition resistance.

Example 4

Catalyst Formulation Using, Other Aluminum Oxide Precursor Solutions

Example 4.1

Nalco-1056 Aluminum Oxide Precursor

A slurry containing 45 wt % solid was prepared according to this procedure:

(A) 264.4 g of a SAPO-34 molecular sieve (wet filter cake, LOI: 45.54%) were added to 179.2 g of deionized water and mixed at 700 RPM for 10 minutes using a Yamato D-4000 mixer (Yamato Scientific America Inc., Orangeburg, N.Y.), then mixed for 3 minutes using a Silverson high-shear mixer model 14RT-A at 6000 rpm (Silverson Machines, Inc., East Longmeadow, Mass.), giving a slurry having a pH value of 6.51 at 30° C.;

(B) A colloidal aluminum oxide solution was prepared by adding 127.2 g of Nalco-1056 colloidal alumina sol containing 4% alumina and 25% silica (Nalco Chemical Company, Naperville, Ill.) to 20 g of a 10% polyvinyl pyrrolidone solution, prepared from PVP 90K (BASF America, Bud Lake, N.J.) and mixing with the Yamato mixer at 700 RPM for 10 minutes, followed with a high shear mixing using the Silverson mixer at 6000 rpm for 3 minutes. This solution had a pH of 3.39 at 29° C.

(C) The colloidal aluminum oxide solution prepared in (B) was combined with the SAPO-34 slurry prepared in (A) while mixing at 700 RPM for 10 minutes with the Yamato mixer. The resulting mixture was then mixed using the Silverson high-shear mixer at 6000 RPM for 3 minutes. This resulted in a slurry having a pH value of 4.47 at 30° C.

(D) 209.2 g of USP Ultrafine kaolin clay (Engelhard Corporation, Iselin, N.J.) were added to the slurry prepared at (C) under mixing at 700 RPM. Mixing at 700 RPM was continued for 10 minutes and was followed with high-shear mixing, using the Silverson high-shear mixer at 6000 rpm for 3 minutes, resulting in a slurry, hereinafter referred to as Slurry 9, having a pH of 4.89 measured at 25° C. Slurry 9 contained 45 wt % solids (on a calcined basis), of which, 40% is SAPO-34, 10.6% is alumina-silica and 49.4% is kaolin clay.

The viscosity of Slurry 9, measured using a Brookfield LV viscometer, using a #3 spindle at 10 rpm, was 3380 centipoise (3.38 Pa-s) at 23° C.

A portion of Slurry 9 (700 g) was spray dried using a Yamato DL-41 spray dryer (Yamato Scientific America, Orangeburg, N.Y.) under the same conditions as in Example 1.1. The spray dried products were calcined in a muffle furnace at 650° C. in air for 2 hours to yield Catalyst 9. The catalyst was submitted to an attrition resistance test. Catalyst 9 gave an ARI of 6.81 wt %/hr Example 4.2

Nalco-8676 Aluminum Oxide Precursor

A slurry containing 45 wt % solid was prepared according to this procedure:

(A) 661.04 g of a SAPO-34 molecular sieve (wet filter cake, LOI: 45.54%) were added to 319.34 g of deionized water and mixed at 700 RPM for 10 minutes using a Yamato D-4000 mixer (Yamato Scientific America Inc., Orangeburg, N.Y.), then mixed for 3 minutes using a Silverson high-shear mixer model L4RT-A at 6000 rpm (Silverson Machines, Inc., East Longmeadow, Mass.), giving a slurry having a pH value of 6.98 at 27° C.;

(B) 450 g of Nalco-8676 colloidal alumina sol containing 10% alumina (Nalco Chemical Company, Naperville, Ill.) was combined with the SAPO-34 slurry prepared in (A) while mixing at 700 RPM for 10 minutes with the Yamato mixer. The resulting mixture was then mixed using the Silverson high-shear mixer at 6000 RPM for 3 minutes. This resulted in a slurry having a pH value of 4.53 at 27° C.

(C) 569.62 g of USP Ultrafine kaolin clay (Engelhard Corporation, Iselin, N.J.) were added to the slurry prepared at (B) under mixing at 700 RPM. Mixing at 700 RPM was continued for 10 minutes and was followed with high-shear mixing, using the Silverson high-shear mixer at 6000 rpm for 3 minutes, resulting in a slurry, hereinafter referred to as Slurry 10, having a pH of 4.28 measured at 25° C. Slurry 10 contained 45 wt % solids (on a calcined basis), of which, 40% is SAPO-34, 5% is alumina and 55% is kaolin clay.

The viscosity of Slurry 10, measured using a Brookfield LV viscometer, using a #3 spindle at 10 rpm, was 240 centipoise (0.24 Pa-s) at 29° C.

A portion of Slurry 10 (700 g) was spray dried using a Yamato DL-41 spray dryer (Yamato Scientific America, Orangeburg, N.Y.) under the same conditions as in Example 1.1. The spray dried products were calcined in a muffle furnace at 650° C. in air for 2 hours to yield Catalyst 10. The catalyst was submitted to an attrition resistance test. Catalyst 10 gave an ARI of 10.88 wt %/hr.

Example 4.3

Aluminum Nitrate Aluminum Oxide Precursor

A slurry containing 40 wt % solid was prepared according to this procedure:

(A) 264.4 g of a SAPO-34 molecular sieve (wet filter cake, LOI: 45.54%) were added to 99.5 g of deionized water and mixed at 700 RPM for 10 minutes using a Yamato D-4000 mixer (Yamato Scientific America Inc., Orangeburg, N.Y.), then mixed for 3 minutes using a Silverson high-shear mixer model L4RT-A at 6000 rpm (Silverson Machines, Inc., East Longmeadow, Mass.), giving a slurry having a pH value of 7.25 at 26° C.;

(B) A solution of aluminum nitrate was prepared by adding 138.2 g of aluminum nitrate (Nalco Chemical Company, Naperville, Ill.) to 49.7 g of deionized water, mixing using the Yamaoto mixer at 700 RPM for 10 minutes, followed with a high-shear mixing using the Silverson mixer at 6000 RPM for 3 minutes. This solution had a pH of 1.4 at 26° C.

(C) The aluminum nitrate solution was combined with the SAPO-34 slurry prepared in (A) while mixing at 700 RPM for 10 minutes with the Yamato mixer. The resulting mixture was then mixed using the Silverson high-shear mixer at 6000 RPM for 3 minutes. This resulted in a slurry having a pH value of 2.24 at 29° C.

(D) 231.2 g of USP Ultrafine kaolin clay (Engelhard Corporation, Iselin, N.J.) were added to the slurry prepared at (C) under mixing at 700 RPM. This gave a very thick slurry, which was diluted by adding 53.8 g deionized water and 61.6 g of 15% ammonia solution, to allow further processing of the slurry. This led to a slurry that was mixed at 700 RPM for 10 minutes, followed with high-shear mixing, using the Silverson high-shear mixer at 6000 rpm for 3 minutes, resulting in a slurry, hereinafter referred to as Slurry 11, having a pH of 3.81 measured at 23° C. Slurry 11 contained 40 wt % solids (on a calcined basis), of which, 40% is SAPO-34, 5.3% is alumina and 54.7% is kaolin clay.

The viscosity of Slurry 11 could not be measured using a Brookfield LV viscometer, using a #3 spindle at 10 rpm.

A portion of Slurry 11 (700 g) was spray dried using a Yamato DL-41 spray dryer (Yamato Scientific America, Orangeburg, N.Y.) under the same conditions as in Example 1.1. The spray dried products were calcined in a muffle furnace at 650° C. in air for 2 hours to yield Catalyst 11. The catalyst was submitted to an attrition resistance test. Catalyst 11 gave an ARI of 10.40 wt %/hr.

Table 5 summarizes the results of the attrition resistance tests obtained for Catalysts 9, 10 and 11. The results of the attrition resistance test show that Catalysts 9, 10 and 11 are far less attrition resistant than any of the catalysts prepared in examples 1, 2 or 3.

TABLE 5

| Slurry | Aluminum oxide precursor | Viscosity* | Spray Dried catalyst | ARI (%/hr) |
|---|---|---|---|---|
| Slurry 9 | Nalco-1056 | 3.380 (23) | Catalyst 9 | 6.81 |
| Slurry 10 | Nalco-8676 | 0.240 (29) | Catalyst 10 | 10.88 |
| Slurry 11 | Aluminum nitrate | — | Catalyst 11 | 10.40 |

*Viscosity in Pa-s, measured at 10 RPM, using a Brookfield LV viscometer, #3 spindle. The measurement temperature in ° C. is indicated between brackets Example 5

Identification of Aluminum Species in Aluminum Oxide Precursor Solutions by NMR Spectroscopy Several aluminum oxide precursor solutions were prepared and analyzed by $^{27}$Al NMR spectroscopy.

Solution A: A solution containing 10.6 wt % aluminum chlorhydrol was prepared by adding 106 g of aluminum chlorohydrate MicroDry (ACH, from Reheis Inc., Berkeley Heights, N.J.) to 984 g of deionized water, and mixed at 700 RPM for 10 minutes using a Yamato 2100 homogenizer (Yamato Scientific America Inc., Orangeburg, N.Y.).

Solution B: 500 g of Solution A was maintained at 40° C. in a water bath, in a sealed polypropylene container for 16 hours.

Solution C: A solution containing 10.6 wt % aluminum chlorhydrol was prepared by diluting 212 g of an aluminum chlorhydrol solution REACH 501 Chlorhydrol 50% (available from Reheis Inc., Berkeley Heights, N.J.) with 788 g of deionized water and mixing at 700 RPM for 10 minutes using a Yamato 2100 homogenizer (Yamato Scientific America Inc., Orangeburg, N.Y.).

Solution D: A solution of NALCO-1056 containing 4% alumina and 26% silica, was purchased from Nalco Chemical Company, Naperville, Ill.

Solution E: A solution of NALCO-8676, containing 10% alumina was purchased from Nalco Chemical Company, Naperville, Ill.

Solution F: A portion of solution E was maintained at 40° C. in a water bath, in a sealed polypropylene container for 16 hours.

Solutions A, B, C, D, E and F were analyzed by $^{27}$Al NMR, using a Bruker DSX 500 NMR spectrometer, with a $^1$H frequency of 500.13 MHz and an $^{27}$Al frequency of 130.31 MHz, using a single 90° (27 Al) pulse and a recycle delay of 1 second.

The $^{27}$Al NMR spectra obtained for Solutions A, B and C under these conditions are shown in FIG. 1. For all three solutions, the NMR spectra exhibit broad peaks at 70 ppm, 11.3 ppm, 10.7 ppm, 0 ppm and −25 ppm, which are indicative of the presence of high and medium molecular weight aluminum species, having in the order of about 80 to about 40 aluminum atoms per molecule. The very sharp peak at 62-63 ppm is characteristic of the tetrahedron $AlO_4$ surrounded by 12 octahedron $AlO_4$ in a structure the same or like aluminum 13-mer ($Al_{13\text{-}mer}$), including $Al_{13\text{-}mer}$ or $Al_{n\text{-}mer}$ (n>13 but oligomers of aluminum having tetrahedron aluminum sites surrounded by octahedron aluminum). The 62-63 ppm signals correspond to the tetrahedron aluminum sites. For Solution B, about 12% of the aluminum atoms are estimated to be in the $Al_{13\text{-}mer}$-structure like state, while, for Solution A, only 4% of the aluminum atoms are estimated to be in the $Al_{13\text{-}mer}$-structure like state. These results show that aging of a fresh solution of aluminum chlorhydrol increases the amount of aluminum species in the $Al_{3\text{-}mer}$-structure like state, responsible for the very sharp peak at 62-63 ppm in $^{27}$Al NMR spectroscopy.

Figure 2:
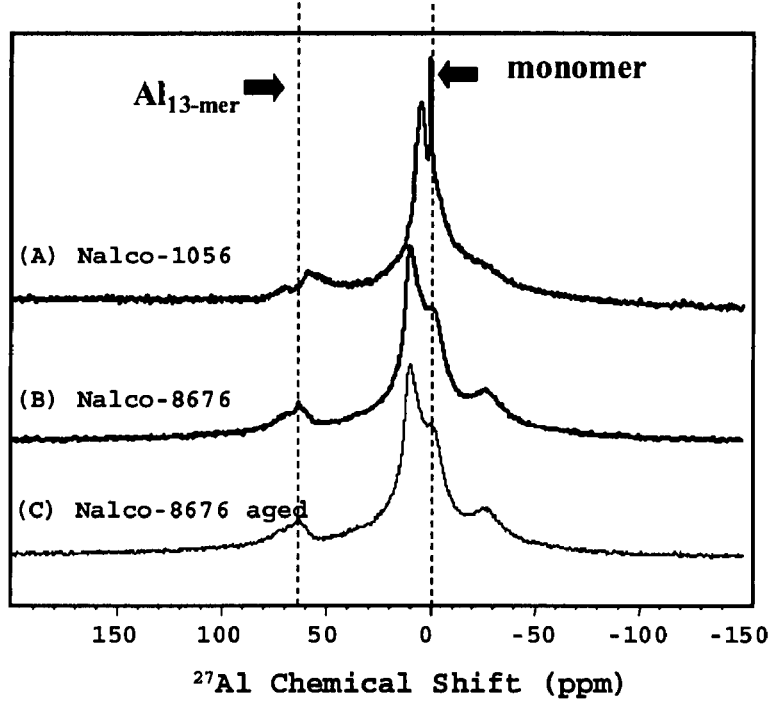
FIG. 2 shows $^{27}$Al NMR spectra of NALCO-1056 and NALCO-8676 solutions prepared with an without aging.

The spectra obtained for Solutions D, E and F are shown in FIG. 2. While a low intensity peak may be seen at 62-63 ppm for Solutions E and F, no such peak can be distinguished in the NMR spectrum of Solution D.

Without wishing to be bound by any theory, it seems that the aluminum species corresponding to the sharp peak at 62-63 ppm in $^{27}$Al NMR is responsible for unique attrition resistance, when used to formulate molecular sieve catalysts. The amount of this aluminum species can be controlled by applying appropriate aging of the aluminum-containing solutions or slurries during catalyst formulation processes. The presence of a sharp peak at 62-63 ppm in $^{27}$Al NMR spectroscopy is a clear indication of the presence of the $AlO_4$ moiety of the $Al_{13\text{-}mer}$ species $[AlO_4Al_{12}(OH)_{24}(H_2O)_{12}]^{7+}$ (see J. J. Fitzgerald and Loren E. Johnson, Journal of Magnetic Resonance 84, 121-133 (1989); J. J. Fitzgerald and A. H.

Rosenberg, Antiperspirants and deodorants, Second Edition, edited by Karl Laden, Marcel Dekker, Inc, (1999)).

Example 5

High Pressure Liquid Chromatography and Relative Binding Efficiency

Several aluminum oxide precursor solutions were prepared and analyzed by high pressure liquid chromatography.

Solution X: A solution containing 50 wt % aluminum chlorhydrol was prepared by adding 250 g of aluminum chlorohydrate MicroDry (ACH, from Reheis Inc., Berkeley Heights, N.J.) to 250 g of deionized water, and mixed at 250 rpm using a Yamato Model 2100 homogenizer (Yamato Scientific America Inc., Orangeburg, N.Y.) until a clear solution was obtained.

Solution Y: 250 g of Solution X was maintained at 40° C. in a water bath, in a sealed polypropylene container for 16 hours.

Solution Z: A commercial ACH solution, Chlorhydrol 50% Solution, Lot. R298-37 was purchased from Reheis Inc., Berkeley Heights, N.J.

Solutions X, Y and Z were submitted to high pressure liquid chromatography analysis. Each sample provided several peaks at different retention times. In this analytical method, the oligomer species with the highest molecular weight elute first and the lowest molecular weight species elute last. The HPLC chromatograms obtained for samples X, Y and Z exhibited several peaks with different peak areas. The data are presented in Table 5, in which P1 through P5 refer to each peak observed, the values between parentheses below P1 through P5 indicate the retention times of each peak and the numbers under the columns labelled P1 through P5 indicate the normalized peak areas. The last column in Table 5 gives the Relative Binding Efficiency (RBE), which corresponds to the ratio of P1, relative to the ratio of P1 for solution X.

TABLE 6

| Solution | P1 (3.88-3.96)* | P2 (3.98-4.01)* | P3 (4.10-4.26)* | P4 (4.51-4.66)* | P5 (>5)* | RBE |
|---|---|---|---|---|---|---|
| X | 42.26 | 43.72 | 7.00 | 6.95 | 0.07 | 1.00 |
| Y | 48.3 | 38.08 | 6.12 | 7.50 | 0.00 | 1.14 |
| Z | 50.33 | 37.02 | 6.67 | 5.97 | 0.01 | 1.19 |

*numbers in parentheses are retention time in minutes

The results presented in Table 5 indicate that aging of a fresh ACH solution increases the RBE, while the commercial ACH solution already has a very high RBE.

While the present invention has been described and illustrated by reference to particular embodiments, those of ordinary skill in the art will appreciate that the invention lends itself to variations not necessarily illustrated herein. For example, it is contemplated that the molecular sieve catalyst composition is useful in the inter-conversion of olefin(s), oxygenate to gasoline conversions reactions, malaeic anhydride, phthalic anyhdride and acrylonitrile formulation, vapor phase methanol synthesis, and various Fischer Tropsch reactions. It is further contemplated that a plug flow, fixed bed or fluidized bed process are used in combination, particularly in different reaction zones within a single or multiple reactor system. It is also contemplated the molecular sieve catalyst compositions described herein are useful as absorbents, adsorbents, gas separators, detergents, water purifiers, and other various uses such as agriculture and horticulture. Additionally contemplated the molecular sieve catalyst compositions include one or more other molecular sieves in combination. For this reason, then, reference should be made solely to the appended claims for purposes of determining the true scope of the present invention.

The invention claimed is:

1. A process for converting a feedstock comprising organic compounds to conversion product which comprises:
   a) forming molecular sieve particles according to the following method:
      i) providing a solution or suspension of an aluminum-containing inorganic oxide precursor, wherein at least 6 atom % of the aluminum in the precursor is in a form exhibiting an $^{27}$Al NMR peak at 62-63 ppm;
      ii) combining the solution or suspension of aluminum-containing inorganic oxide precursor with a molecular sieve to form a catalyst formulation slurry; and
      iii) forming molecular sieve catalyst particles from the catalyst formulation slurry, such that the catalyst particles contain from 40% to about 60% by weight of molecular sieve and have an attrition resistance index of less than 0.5 wt%/hr; and
   b) contacting said feedstock with a catalyst comprising an active form of said molecular sieve catalyst particles.

2. The process of claim 1, wherein said feedstock comprises oxygenates and said conversion product comprises one or more olefins.

3. A process for converting a feedstock comprising organic compounds to conversion product which comprises:
   a) providing a molecular sieve catalyst comprising:
      a silicoaluminophosphate molecular sieve;
      a mixed aluminum-zirconium precursor capable of conversion to a aluminum-zirconium oxide;
      a clay; wherein the catalyst has an ARI of less than 1.0.
   b) contacting said feedstock with an active form of said molecular sieve catalyst.

4. The process of claim 3, wherein said feedstock comprises oxygenates and said conversion product comprises one or more olefins.

5. The method of claim 1, wherein the provided solution or suspension is further analyzed by $^{27}$Al NMR spectroscopy to determine the atom% of the aluminum in the precursor.

* * * * *